(12) United States Patent
Shimohirao et al.

(10) Patent No.: US 10,918,753 B2
(45) Date of Patent: Feb. 16, 2021

(54) USE OF OZONE TO CONTROL BIOBURDEN IN PRECIPITATED CALCIUM CARBONATE SLURRY (PCC)

(71) Applicant: Colgate-Palmolive Company, New York, NY (US)

(72) Inventors: Nilza Shimohirao, Sao Paulo (BR); Mohamad Bazazan, Pittstown, NJ (US); Erico Prat, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 315 days.

(21) Appl. No.: 15/528,604

(22) PCT Filed: Dec. 1, 2014

(86) PCT No.: PCT/US2014/067980
§ 371 (c)(1),
(2) Date: May 22, 2017

(87) PCT Pub. No.: WO2016/089358
PCT Pub. Date: Jun. 9, 2016

(65) Prior Publication Data
US 2017/0274109 A1 Sep. 28, 2017

(51) Int. Cl.
| | | |
|---|---|---|
| C02F 1/78 | (2006.01) |
| A61L 2/20 | (2006.01) |
| A61L 9/015 | (2006.01) |
| B01F 5/04 | (2006.01) |
| B01F 3/04 | (2006.01) |
| B01F 3/20 | (2006.01) |
| A01N 59/00 | (2006.01) |
| C02F 11/08 | (2006.01) |
| A61K 8/19 | (2006.01) |
| A61Q 11/00 | (2006.01) |
| C01F 11/18 | (2006.01) |

(52) U.S. Cl.
CPC .............. *A61L 2/202* (2013.01); *A01N 59/00* (2013.01); *A61K 8/19* (2013.01); *A61Q 11/00* (2013.01); *C01F 11/181* (2013.01); *C02F 11/08* (2013.01); *A61K 2800/805* (2013.01); *C02F 2303/04* (2013.01)

(58) Field of Classification Search
CPC . C02F 1/78; A01N 65/00; A61P 31/04; C04B 28/02
See application file for complete search history.

(56) References Cited

U.S. PATENT DOCUMENTS

| | | | | |
|---|---|---|---|---|
| 4,793,985 A * | 12/1988 | Price | ............. | B01F 3/1221 106/465 |
| 5,147,563 A * | 9/1992 | Long, Jr. | ............. | B01F 3/0473 210/758 |
| 5,647,895 A * | 7/1997 | Drew | ............. | A61L 2/04 106/15.05 |
| 2003/0082091 A1* | 5/2003 | Jasra | ............. | C01F 11/18 423/432 |
| 2003/0143164 A1* | 7/2003 | Lynch | ............. | A61K 8/22 424/52 |
| 2008/0213125 A1* | 9/2008 | Boast | ............. | A61L 2/202 422/2 |
| 2012/0276023 A1 | 11/2012 | Shimohirao et al. | | |
| 2013/0189200 A1* | 7/2013 | Shiba | ............. | A61K 8/22 424/53 |

FOREIGN PATENT DOCUMENTS

| | | | | |
|---|---|---|---|---|
| WO | WO 2006/002406 | 1/2006 | | |
| WO | WO 2011/075662 | 6/2011 | | |
| WO | WO-2012175490 A1 * | 12/2012 | ............. | C01F 11/181 |

OTHER PUBLICATIONS

Case Medica Inc., "The Basics of Sterilization" http://www.casemed.com/caseacademy/downloads/CASDF003.pdf Retrieved from website Sep. 11, 2014.
International Search Report and Written Opinion in International Application No. PCT/US2014/067980, dated Jan. 29, 2015.
Smithee, 2012, "Cooling Tower Maintenance Improves with Ozone," www.ozonesolutions.com/info/cooling-tower-maintenance-improves-with-ozone.
U.S. Coast Guard Research and Development Center, 2004, "Evaluation of Biocides for Potential Treatment of Ballast Water, Final Report," Report No. CG-D-01-05, National Technical Information Service, Springfield, VA.

\* cited by examiner

*Primary Examiner* — Tracy Liu

(57) ABSTRACT

The present disclosure is directed to a method for reducing bacteria in a precipitated calcium carbonate ($CaCO_3$) slurry, the method including: adding water to calcium oxide (CaO) to form $Ca(OH)_2$; treating the $Ca(OH)_2$ with $CO_2$ gas to form a slurry including precipitated $CaCO_3$; neutralizing the slurry; and exposing the slurry that was neutralized to ozone in an amount sufficient to reduce bacteria in the precipitated calcium carbonate slurry. Oral care compositions including the precipitated calcium carbonate of the disclosed process are also described.

17 Claims, 3 Drawing Sheets

USE OF OZONE TO CONTROL BIOBURDEN IN PRECIPITATED CALCIUM CARBONATE SLURRY (PCC)

BACKGROUND

Precipitated calcium carbonate or PCC is manufactured on a commercial scale for use in a variety of industrial, cosmetic and pharmaceutical products. Generally, precipitated calcium carbonate is made by heating crushed limestone at high temperatures and then breaking the raw calcium carbonate into lime (CaO) and carbon dioxide gas ($CO_2$). Addition of water to the lime (a process called "slaking") yields $Ca(OH)_2$. The slaked lime (or "milk of time") is treated with carbon dioxide gas. The resulting calcium carbonate precipitates from the aqueous solution, yielding a slurry of precipitated calcium carbonate, which is then neutralized and dried.

Slurries of precipitated calcium carbonate are susceptible to bacteria. Methods known in the art to reduce bacteria, for example in food, cosmetics or substrates, such as medical equipment, are known in the art. Sterilization and pasteurization are two such well known methods. A typical sterilization procedure requires a heat treatment, generally ranging from about 120° C.-134° C., for a period of about one hour. Shorter sterilization times, for example, sterilization times of about 15 minutes at 121° C. require pressures of about 15 psi. Pasteurization, which may be used to cultivate thermophilic bacteria that may guard against other contaminants, involves a heat treatment ranging from about 60° C. to about 82° C. for at least one hour. Such processes require special equipment, energy for heat, and adequate time for heating and cooling.

Antibiotics such as poly[(hexamethylene)biguanide] (PHMB), can be added to the slurry to reduce the amount of bacteria. However, such antibiotics, while effective against gram negative bacteria, are not as effective in destroying many of the grain positive bacteria. Further, these and other antibiotics are not decomposed after use and, accordingly, may remain active in products produced using the dried precipitated calcium carbonate, which may be undesirable in some applications.

Ozone, which is capable of effectively killing gram negative and gram positive bacteria and which decomposes rapidly, has been reported to be effective for some clinical uses, such as ozone sterilization of medical equipment. However, in such applications, the cycle time may be lengthy, e.g., 4.5 hours.

Further, ozone has not been contemplated for use in PCC slurries, likely because of the high concentration of solids in the slurry. For example, it has been reported that water having a high mineral content is generally not conducive to effective treatment using ozone. Further, in some instances where water to be treated has an excess of 500 ppm of $CaCO_3$, the use of ozone has been precluded. See Smithee, Brian PE, CPE "Cooling Tower Maintenance Improves with Ozone", Apr. 19, 2012 on the world wide web at ozonesolutions.com/info/cooling-tower-maintenance-improves-with-ozone. See also U.S. Coast Guard Research and Development Center, Report No. CG-D-01-05, "Evaluation of Biocides for Potential Treatment of Ballast Water, Final Report," National Technical Information Service, Springfield, Va., October, 2004.

Accordingly, there remains a need in the art to develop processes and systems for reducing the amount of bacteria in a precipitated calcium carbonate slurry, which are capable of killing a wide range of bacteria, do not require special equipment or lengthy time periods and are readily degraded or easily removed before using the precipitated calcium carbonate in industrial, cosmetic and/or pharmaceutical products.

BRIEF SUMMARY

The present disclosure is directed to processes and systems for reducing bacteria in a precipitated calcium carbonate ($CaCO_3$) slurry, the process including: adding Water to calcium oxide (CaO) to form $Ca(OH)_2$; treating the $Ca(OH)_2$ With $CO_2$ gas to form a slurry including precipitated $CaCO_3$; neutralizing the slurry; and exposing the slurry that was neutralized to ozone in an amount sufficient to reduce bacteria in the precipitated calcium carbonate slurry.

The present disclosure also includes oral care compositions, which include the precipitated $CaCO_3$ prepared according to the described processes.

Further areas of applicability of the present invention will become apparent from the detailed description provided hereinafter. It should be understood that the detailed description and specific examples, while indicating a typical embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the disclosed embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, an references cited herein are hereby incorporated b referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Figure 1:
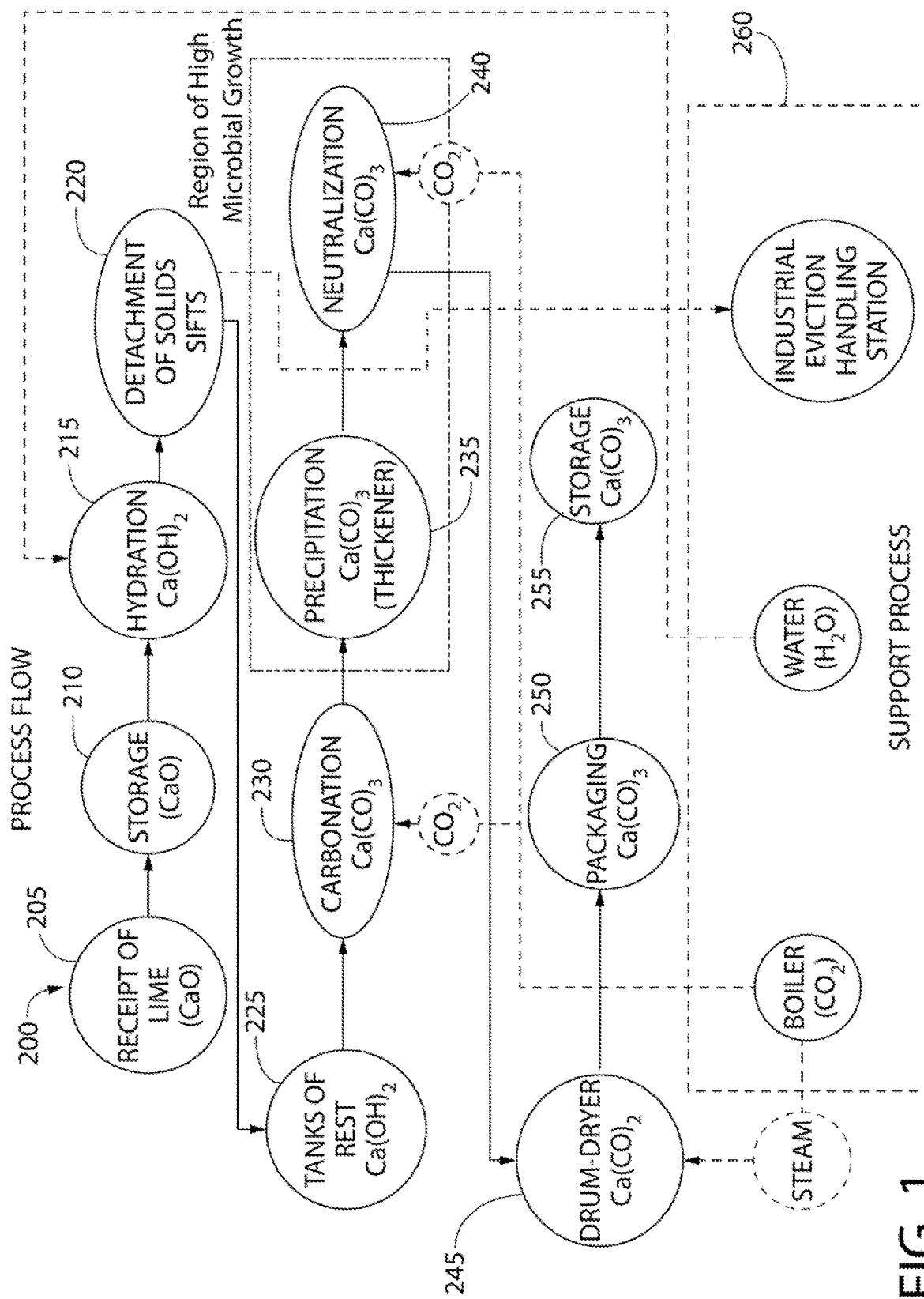
FIG. 1 depicts an example of a process flow for preparing precipitated calcium carbonate consistent with the embodiments of the invention.

The present disclosure is directed to a process for reducing an amount of bacteria in a precipitated calcium carbonate ($CaCO_3$) slurry using ozone. FIG. 1 depicts an embodiment of a process 200 for preparing precipitated calcium carbonate. As shown in this embodiment, precipitated calcium carbonate is prepared by adding water (215) to CaO (205, 210) to yield $Ca(OH)_2$. After removal of the solids by sifting (220, 225), $Ca(OH)_2$ is treated with carbon dioxide gas (230) resulting in a slurry (235), which may be treated with or exposed to ozone, as described herein. Support agents, such as water and carbon dioxide gas, which are used by the process 200 may be produced by a support process 260, as shown in the example of FIG. 1.

As used herein, "slurry" refers to precipitated calcium carbonate in water. The term "biocide" as used herein refers to a chemical substance which can deter, render harmless, or exert a controlling effect on any harmful organism by chemical or biological means. In some embodiments, ozone is used as a biocide.

In various embodiments, the slurry is neutralized (240). In some embodiments, neutralization (240) may be accomplished by injection of carbon dioxide. The carbon dioxide for neutralization may be introduced at a flow rate ranging from, for example, about 10 to about 100 m$^3$/h, front about 40 to about 100 m$^3$/h and more typically from about 60 to about 80 m$^3$/h.

In some embodiments, a typical pressure for neutralization is from about 1 to about 5 kg/cm$^3$, more typically from about 1 to about 4 kg/cm$^3$, and most typically from about 1.5 to about 3.5 kg/cm$^3$. The slurry is neutralized for a period of time ranging from about 25 minutes to about 50 minutes, more typically from about 30 minutes to about 40 minutes.

In other embodiments, the slurry may be neutralized using an acid such as a mineral acid (phosphoric, sulfuric, nitric, and/or hydrochloric, for example) or an organic acid, such as acetic, propionic or sulfonic acid.

After neutralization, the slurry is then optionally subjected to a drying process that may be performed with, for example, any art recognized dryer (245). Suitable dryers for use in accordance with the present disclosure include drum dryers. In some embodiments, the slurry is dried at a temperature ranging from about 100° C. to about 150° C., from about 110° C. to about 140° C., or, more typically, at a temperature ranging from about 115° C., to about 125° C. The drying, time depends on the quantity of product to be dried and the product humidity to be achieved. Appropriate drying times are readily apparent to the skilled artisan.

The resulted dried precipitated $CaCO_3$ may then be subsequently packaged (250) and stored (255) for use in oral care composition products, such as a dentifrice. The oral care composition may be in the form of a paste, cream, mousse, gel, powder wash, or the like. The oral care composition in certain embodiments includes the dried precipitated $CaCO_3$ combined with one or more other oral care ingredients such as humectants, inorganic dispersants, bicarbonate salts, pH modifying agents, surfactants, foam modulators, thickening agents, viscosity modifiers, sweeteners, colorants, anti-caries agents, anti-calculus agents, stannous ion sources, zinc ion sources, breath fresheners, antiplaque agents, enzymes, vitamins, anti-adhesion agents and combinations thereof.

In some embodiments, there is no difference in taste between an oral care composition comprising precipitated $CaCO_3$ using the ozone treatment method disclosed herein and an oral composition comprising precipitated $CaCO_3$ without using the present ozone treatment method.

Figure 2:
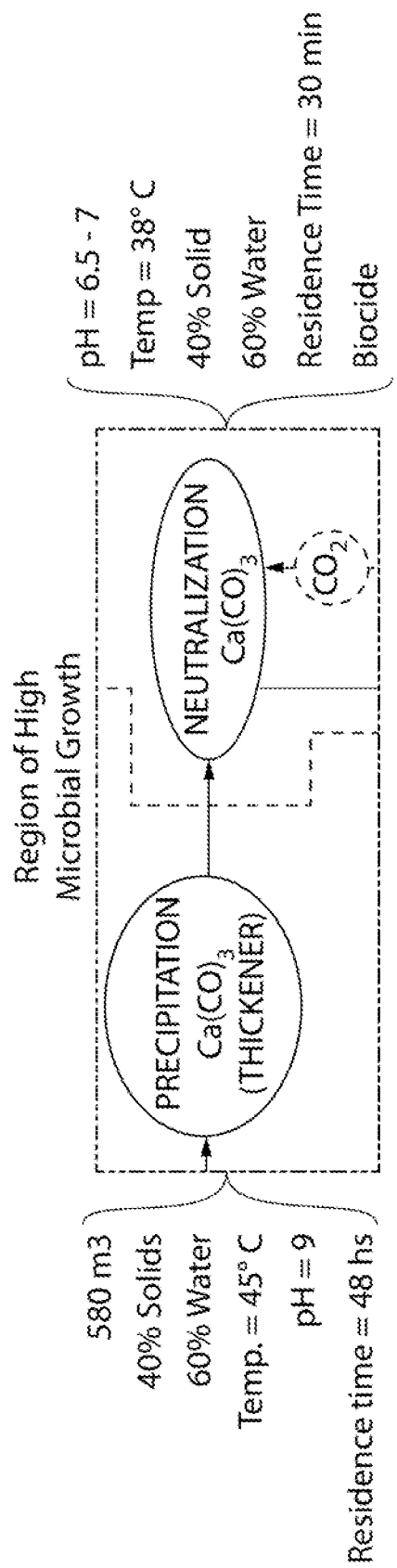
FIG. 2 is a diagram that highlights the portion of the exemplary process flow that is susceptible to bacterial contamination.

As also indicated in FIG. 1, the precipitated calcium carbonate slurries are susceptible to bacteria, particularly during the precipitation (235) and neutralization (240) phases of the process 200, (labelled the "Region of High Microbial Growth", in FIG. 1). FIG. 2 depicts characteristics of the Region of High Microbial Growth in one embodiment. As shown in FIG. 2, the precipitation phase occurs in a 580 m$^3$ tank. The precipitation phase contains about 40% w/w solids and 60% water, and is at a temperature of 45° C., and a pH of 9. The residence time for the slurry during the precipitation phase is about 48 hours. As used herein "residence time" or "removal time" is the average amount of time that a particle spends in a particular part of the system or phase of the process. Accordingly, a residence time of 48 hours is the amount of time the slurry is in the precipitation phase (235) before transfer to the neutralization phase (240) in the example shown.

FIG. 2 also describes an embodiment of the slurry characteristics during the neutralization phase (240). In this embodiment, the pH of the slurry during neutralization is about 6.5 to 7 and the temperature is about 38° C. with a percent of solids of about 40% w/w. FIG. 2 also describes the residence time for a biocide, which according to some embodiments may be about 30 minutes under recirculation.

According to one embodiment of the disclosure, the slurry is exposed to or contacted with ozone via a recirculation loop during the neutralization phase (240). It will be understood that, in this embodiment, there is a flow of the slurry out of a neutralization tank, for example, past at least an inlet for the addition of ozone, as an example of a biocide, then back into the neutralization tank. It is further to be understood that the flow through this recirculation loop may occur continuously during the entire ozone treatment. Alternatively, the flow may be suspended for one or more periods whenever needed, such as when needed in order to control reaction conditions of the ozone treatment. The residence time for ozone under recirculation may range from about 15 minutes to about 50 minutes. More typically, from about 20 minutes to about 40 minutes, even more typically from about 30 minutes to about 40 minutes. In some embodiments, the amount of time the ozone is contacted with the slurry under recirculation is about 30 minutes.

In some embodiments, ozone can be contacted with or added to the precipitated calcium carbonate during the neutralization phase (240) to reduce the number of viable bacteria in the slurry. In other embodiments, ozone can be contacted with or added to the precipitated calcium carbonate after the neutralization phase (240) to reduce the number of viable bacteria in the slurry. In various embodiments, the slurry is exposed to ozone in a manner and/or amount sufficient to reduce bacteria in the slurry: e.g., sufficient to kill or inactivate bacteria. In Various embodiments, the ozone is added during the initial preparation of the PCC; after precipitation (225) (e.g. from carbonation of the slaked lime) and after neutralization (240), but before the initial drying (245). More specifically, the ozone may be added after the calcium hydroxide solution is treated with an excess of carbon dioxide, thereby forming the PCC and after the PCC is neutralized with $CO_2$.

In some embodiments, the pH of the slurry treated with ozone during neutralization ranges from about 6.9 to about 8.5, such as between about 6.5 to about 7.0. In some embodiments, the of the slurry treated with ozone after neutralization ranges from about 6.9 to about 8.5, more typically between about 6.5 to about 7.0.

As used herein, the term "ozone" or "$O_3$" refers to a chemical structure having the following formula:

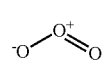

(I)

In some embodiments, the ozone is injected or introduced into the slurry in gaseous form. In various embodiments, ozone gas is produced in a corona discharge-based generator from air or high purity oxygen may be used. In some embodiments, a commercially available ozone generator is used, for example, corona discharge ozone generators available from the Ozonia, company of Leonia, N.J. In other embodiments, ozone is produced by high-intensity ultraviolet (UV) light or by a high-voltage electric field.

In some embodiments, the ozone dissolves in the slurry after the ozone is mixed with or otherwise exposed to the slurry. In various embodiments, the ozone does not remain in the slurry after residence tune with the bacteria that are in the slurry, but decomposes into oxygen. Without being bound by theory, the half life of the ozone in the slurry may vary depending upon temperature, pH, concentration and type of solutes. Generally, however, the half life of ozone in the slurry ranges from about 2 hours to about a few seconds and more typically about 20-60 minutes.

In some embodiments, the temperature of the slurry treated with ozone ranges from about 20° C. to about 50° C., more typically from about 25° to about 47° C., or even more typically from about 25° C. to about. 38° C.

In various embodiments, the slurry can have a solid content ranging, for example, from about 1% w/w to about 50% w/w solids, for example about 10% w/w to about 40% w/w solids, and further, for example, from about 15% w/w to about 25% w/w solids.

In the some embodiments, the ozone is added into the slurry at a concentration sufficient to provide anti-bacterial activity. For example, the concentration of ozone in the gas phase ranges from about 3.5 ppm to about 30 ppm or about 3.5 ppm to about 28 ppm. In other embodiments, the concentration of ozone in the gas phase ranges from about 4.0 ppm to about 26 ppm. In yet other embodiments, the concentration of ozone in the gas phase ranges from about 5.0 ppm to about 25 ppm. In yet further embodiments, the concentration of ozone in the gas phase is about 25 ppm.

In the present disclosure, the ozone-based slurry treatment process depends upon transfer of ozone from the gas phase to the slurry for oxidation of the bacteria, which kills or otherwise inactivates the bacteria. In some embodiments, a bubble column is used to expose the slurry to the ozone and effect the transfer. Bubble columns comprise a large column or basin and gas diffusers located at the bottom of the column or basin. The column or basin is filled with the slurry and ozone gas is introduced through the gas diffusers. Fine bubbles of ozone gas rise through the slurry in the column or basin, which promotes dissolution of the ozone into the slurry.

In yet other embodiments, ozone may be transferred to the slurry by the use of an injector that exposes the slurry to the ozone, such as a venturi injector, in which slurry flows through the venturi and ozone gas is injected at the throat of the venturi. In some embodiments, static mixers can be used downstream from the injector to achieve additional mixing and exposure of ozone in the slurry. Bubble columns, venturi injectors and/or static mixers are well known in the art and commercially available, e.g., Ozone Solutions Inc., Hull, Iowa, Lenntech BV, Delft, Neatherlands.

Figure 3:
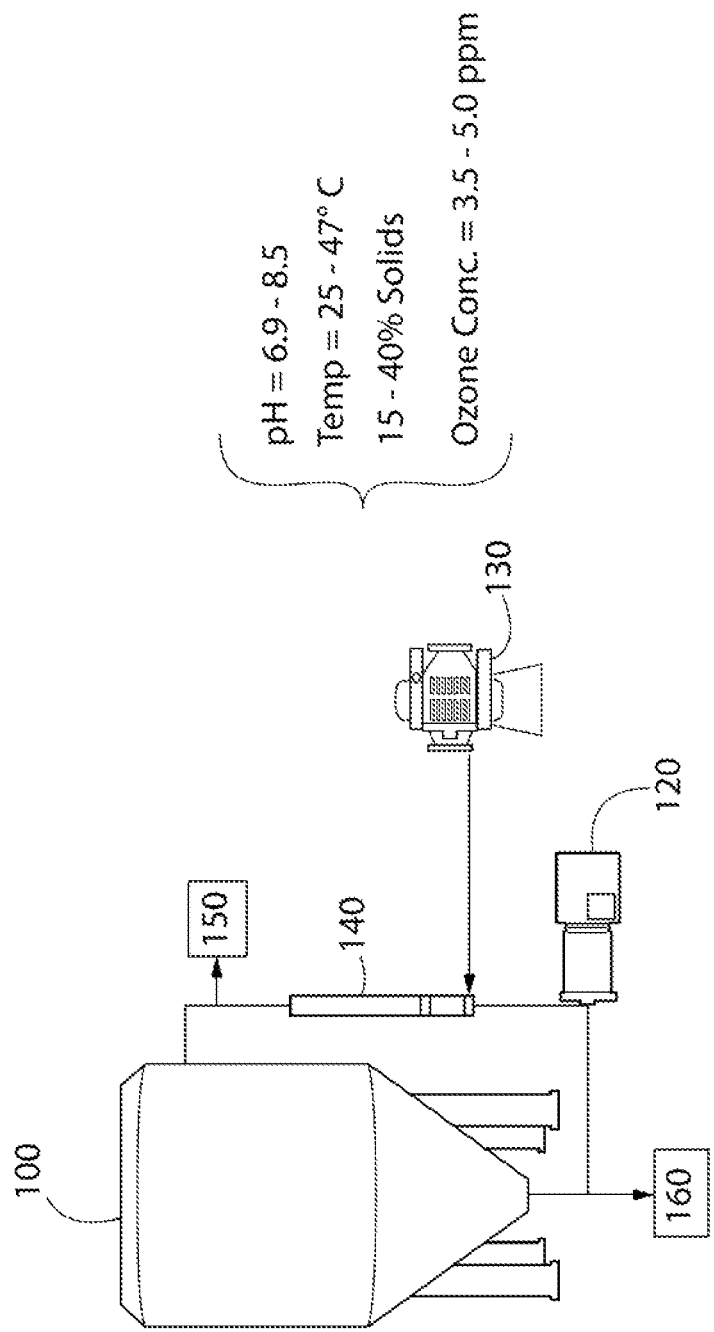
FIG. 3 depicts an embodiment for ozone exposure and sampling of a precipitated calcium carbonate slurry consistent with the principles of the invention.

FIG. 3 depicts an embodiment for exposing slurry to ozone. In this embodiment, a neutralization tank (100) containing slurry is shown. In this embodiment, the solid content of the slurry ranges from 15% w/w-40% w/w and has a pH and a temperature ranging from 6.9 to 8.5 and 25° C. to 47° C., respectively. The slurry is transferred via a recirculation loop (110) from the neutralization tank (100) to a venturi injector (not shown) using a pump (120). Ozone is introduced into the slurry via the venture injector (not shown), which is connected to an ozone generator (130). The mixture of slurry and ozone is then transferred to a static mixer (140), where the slurry and ozone are further mixed. In this embodiment, the static mixer is shown as being in a typical vertical position, parallel to the neutralization tank. In other embodiments, the static mixer may be in a horizontal position, perpendicular to the neutralization tank.

After the ozone-exposed slurry passes through the static mixer (140), the slurry is then transferred back into the neutralization tank (100). In some embodiments, the ozone-treated slurry is mixed with untreated slurry from the precipitation phase (not shown) in the neutralization tank (100). In such embodiments, the ozone-treated and untreated slurry are then recirculated or circulated, respectively, through the pump (120), through ozone injection from the ozone generator (130) through the static mixer (140) and then back into the neutralization tank (100).

FIG. 3 also depicts two embodiments of sampling points. As used herein "sampling point" refers to the point in the process of the present disclosure where slurry is sampled to assess the effect of the ozone treatment on the reduction of live bacteria in the slurry. Sampling point 1 (160) shows that a sample of slurry may be taken after the ozone treatment and after recirculation of the slurry through the neutralization tank (100). In another embodiment, the sample is taken immediately after the ozone is mixed with the slurry in the static mixer (140), i.e., sampling point 2 (150). In some embodiments, both sampling points may be used.

In various embodiments, the amount of time the ozone is contacted with the slurry before the slurry is sampled to assess a reduction in the amount of bacteria in the slurry may range from about a few seconds to about 40 minutes. More typically, the time ranges from about 25 seconds and about 30 minutes or from about 20 seconds to about 25 minutes, or from about 10 seconds to about 20 minutes and even more typically about 3-10 seconds. In some embodiments, the amount of time the ozone is contacted with the slum before the slurry is sampled is from 30 minutes to 40 minutes.

For example, when the slurry is sampled from sampling point 1 (160), the time the ozone is in contact with the slurry is between about 30 minutes and 40 minutes under recirculation. In other embodiments, for example, when the slurry is sampled from sampling point 2 (150), the ozone is in contact with the slurry from about 2 seconds to about 15 seconds, typically about 3 seconds to about 10 seconds.

In some embodiments, a sample of the slurry is taken before and after ozone treatment to assess the effect of the ozone treatment on the bioburden. As used here, "bioburden" refers to the degree of bacterial contamination or bacterial load. In some embodiments, the ozone used in the present processes is introduced in an amount and/or manner that is able to reduce the amount of bacteria present in the slurry. Without being limited by theory, ozone can break cell membranes or protoplasm, killing or otherwise inactivating bacteria.

"Bacteria" as used herein include gram-negative and gram-positive bacteria. Gram-positive bacteria are a class of bacteria that take up the crystal violet stain used in the Gram staining method of bacterial differentiation. The thick peptidoglycan layer in the cell wall that encases their cell membrane retains the stain, making definitive identification possible. Examples of gram positive bacteria include but are not limited *Staphylococcus, Streptococcus, Enterococcus, Bacillus, Corynebacterium, Nocardia* and *Actinobacteria*.

Gram-negative bacteria cannot retain the violet stain after the decolorization step; alcohol used in the decolorization process degrades the outer membrane of gram-negative cells making the cell wall more porous and incapable of retaining the crystal violet stain. Their peptidoglycan layer is much thinner and sandwiched between an inner cell membrane and a bacterial outer membrane, causing them to take up the counterstain (safranin or fuchsine) and appear red or pink. Examples of gram negative bacteria include, but are nut limited to Escherichia coli (E. coli), Salmonella, Shigella, Enterobacter, Klebsiella, Serratia, Pseudomonas, Moraxella, Helicobacter, Stenotrophomonas, Bdellovibrio, Providencia and Burkholderia. Other notable groups of gram-negative bacteria include the cyanobacteria, spirochaetes, green sulfur, and green non-sulfur bacteria.

As described herein, the ozone used in the disclosed process is capable of reducing the bioburden of the slurry by several degrees, including by about a 1-log reduction, about a 2-log reduction, about a 3-log reduction, about a 4-log reduction, about a 5-log reduction, about a 6-log reduction, about a 7-log reduction, about an 8-log reduction, about a 9 log reduction or about, a 10-log reduction. As used herein, the phrase "log reduction" is used to describe the relative number of live bacteria eliminated from the slurry after ozone treatment, e.g., a "5-log reduction" means lowering the number of live or active bacteria by 100,000-fold.

In some embodiments, the bioburden is reduced to a level of less than $10^2$ Colony Forming Units per gram ((CFU)/g). In other embodiments, the bioburden level is reduced to a level of $10^1$ CFU/g maximum. In yet further embodiments, the bioburden is reduced to a level of less than 10 CFU/g.

In various embodiments, the amount of time the ozone is contacted with the slurry before the shiny results in about a 1 log reduction, about a 2 log reduction, about a 3 log reduction, about a 4 log reduction, about a 5 log reduction, about a 6 log reduction, about a 7 log reduction, about an 8 log reduction, about a 9 log reduction or about a 10 log reduction or more of bacteria may range from about a few seconds to about 40 minutes. More typically, the time ranges from about 25 seconds to about 30 minutes or from about 20 seconds to about 25 minutes, or from about 10 seconds to about 20 minutes and even more typically about 3 seconds to about10 seconds. In some embodiments, the amount of time the ozone is contacted with the slurry before the slurry results in about a 1 log reduction, about a 2 log reduction, about a 3 log reduction, about a 4 log reduction, about a 5 log reduction, about a 6 log reduction, about a 7 log reduction, about an 8 log reduction, about a 9 log reduction or about a 10 log reduction or more of bacteria is from about 30 minutes to about 40 minutes.

In some embodiments, the amount of time the ozone is contacted with the slurry before the slurry results in about a 5 log reduction or more of bacteria is about 30 minutes or less.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Example 1

Ozone Treatment and Sampling at Sampling Point 1 (160)

A precipitated calcium carbonate slurry was prepared as shown FIG. 1. At the precipitation phase of the "Region of High Microbial Growth", FIG. 1), the slurry was contaminated with gram negative and gram positive bacilli. The shiny was then continuously transferred from a precipitation tank (not shown) to a neutralization tank (100). Upon entry into the neutralization tank, the slurry was neutralized using carbon dioxide. A sample was collected from the neutralization tank to assess the initial bioburden of the slurry ($3.6 \times 10^6$ CFU/g). After neutralization, 3.5 or 5 ppm (depending on trial) of ozone was injected into the slurry after circulation through the pump (120) (FIG. 3). Four trials were conducted and the results are shown in Table 1. As shown in Table 1, the percent FCC (solid content) in the neutralization tank ranged from 12%-39%. The pH of the slurry in the neutralization tank ranged from 6.9 to 8.3 and the temperature ranged from 24° C. to 46° C.

The degree of log reduction in bacteria was sampled at sampling point 1 (160) (FIG. 3) at time zero and every five minutes up to 40 minutes. As depicted in Table 1, below, a 1-2 log reduction of bacteria was observed after 40 minutes under recirculation.

TABLE 1

| Trial | Sampling Point | Ozone (ppm) | % PCC | pH | Temp (° C.) | Log Reduction |
| --- | --- | --- | --- | --- | --- | --- |
| T1 | 1 | 5.0 | 12 | 8.3 | 24 | 2 log |
| T2 | 1 | 5.0 | 28 | 7.2 | 33 | 2 log |
| T3 | 1 | 3.5 | 39 | 6.9 | 33 | 1 log |
| T4 | 1 | 5.0 | 39 | 6.9 | 46 | 2 log |

Example 2

Ozone Treatment and Sampling at Sampling Point 1 (160) and Sampling Point 2 (150)

A precipitated calcium carbonate slurry was prepared according to Example 1. Five trials were conducted. The ozone was injected as described in Example 1 at a concentration ranging from 5 ppm to 25 ppm. Samples were taken at sampling point 1 (160) or sampling point 2 (150) as shown in FIG. 3. Samples were taken after 40 minutes of recirculation, 40 minutes after ozone contact with the slurry in the neutralization tank (100) or immediately after the slurry passed through the static mixer (140) as shown in FIG. 3. As is evident from Table 2, a higher ozone injection (25 ppm) resulted in a greater log reduction of bacteria (4-5 log-reduction) than the use of lower concentrations of injected ozone (1-2 log reduction). In addition, a sample obtained from sampling point 2 (150) demonstrated a higher log-reduction in bacteria than samples taken from sampling point 1 (160). This difference is log reduction may be attributable to the mixing of ozone-treated slurry in the neutralization tank (100) with the non-treated slurry from the precipitation tank (not shown).

TABLE 2

| Trial | Sampling Point | Ozone concentration (ppm) | Slurry Transfer Flow | pH | Time | Log Reduction |
| --- | --- | --- | --- | --- | --- | --- |
| T1 | 1 | 7.5 | Recirculation | 8.3 | 40 minutes | 2 log |
| T2 | 1 | 7.5 | Recirculation | 7.2 | +40 minutes | +2 log |
| T3 | 1 | 5 | Within Tank | 6.9 | 40 minutes | 1 log |

TABLE 2-continued

| Trial | Sampling Point | Ozone concentration (ppm) | Slurry Transfer Flow | pH | Time | Log Reduction |
|---|---|---|---|---|---|---|
| T4 | 1 | 25 | Recirculation | 6.9 | 40 minutes | 2 log |
| T5 | 2 | 25 | After initial flow through static mixer | 6.9 | seconds | 4-5 log |

Example 3

Ozone Treatment and Further Sampling at Sampling Points 1 (160) and 2 (150)

The sampling variability was confirmed in further trials by assessing the ozone concentration before and after ozone treatment and assessing the bioburden from samples taken at sampling point 1 (160) or sampling point 2 (150). In one trial, an initial bioburden (without ozone) of a sample collected from the slurry tank was $3.6 \times 10^6$ CFU/g. After an ozone injection at a 5 ppm concentration, the amount of bioburden was reduced to $1.7 \times 10^4$ CFU/g after 40 minutes recirculation. Sampling at sampling point 2 (150), however, revealed a bioburden of only $9.1 \times 10^1$ CFU/g. Another trial demonstrating an initial bioburden of $8.8 \times 10^5$ CFU/g (no ozone treatment), was shown to have a low bioburden of $7.0 \times 10^1$ CFU/g when assessed at sampling point 2 (150), (sampled seconds after ozone injection). A third trial demonstrated that after ozone treatment and 40 minutes recirculation, the bioburden was $8.8 \times 10^5$ CFU/g when sampled at sampling point 1 (160), which is after the ozone-treated slurry is further mixed with untreated slurry. However, when a sample in the third trial was collected and tested at sampling point 2 (150) a few seconds after ozone injection, the bioburden was less than 10 CFU/g. Accordingly, the data support that the disclosed process using ozone treatment is capable of reducing an initial bioburden by 5 log, i.e., $10^6$ to $10^1$ CFU/g.

What is claimed is:

1. A method for reducing bacteria in a precipitated calcium carbonate ($CaCO_3$) slurry, the method comprising:
    adding water to calcium oxide (CaO) to form $Ca(OH)_2$;
    treating the $Ca(OH)_2$ with $CO_2$ gas to form a slurry comprising precipitated $CaCO_3$;
    neutralizing the slurry; and
    exposing the slurry that was neutralized to ozone in an amount sufficient to reduce bacteria in the precipitated calcium carbonate slurry,
    wherein a solid concentration of precipitated $CaCO_3$ in the slurry ranges from about 12% w/w to about 40% w/w;
    wherein the concentration of ozone in the neutralized slurry ranges from about 5 ppm to about 25 ppm.

2. The method of claim 1, wherein the exposing comprises injecting ozone gas into the slurry that was neutralized.

3. The method of claim 1, wherein the method further comprises:
    mixing the slurry that was neutralized and the ozone to create a mixture; and
    recirculating the mixture into a tank.

4. The method of claim 3, wherein the method further comprises sampling the slurry after the mixing and before the recirculating to determine a degree of reduction of the bacteria.

5. The method of claim 3, wherein the mixing comprises mixing the slurry and the ozone using a static mixer.

6. The method of claim 1, wherein a log reduction of the bacteria ranges from about a 1 log reduction to about a 5 log reduction.

7. The method of claim 1, wherein a log reduction of the bacteria ranges from about a 4 log reduction to about a 5 log reduction.

8. The method of claim 1, wherein a concentration of ozone in the slurry that was neutralized is about 25 ppm.

9. The method of claim 1, wherein the bacteria comprise gram positive bacteria.

10. The method of claim 1, wherein the method further comprises:
    sampling the slurry that was neutralized before exposing the slurry to ozone;
    assessing a bioburden before exposing the slurry to ozone;
    sampling the slurry that was neutralized after exposing the slurry to ozone; and
    assessing a bioburden after exposing the slurry to ozone.

11. The method of claim 10, wherein the sampling the slurry that was neutralized after exposing the slurry to ozone occurs about 10 seconds to about 40 minutes after the slurry was exposed to ozone.

12. The method of claim 10, wherein the sampling the slurry that was neutralized after exposing the slurry to ozone occurs about 3 seconds to about 10 seconds after the slurry was exposed to ozone.

13. The method of claim 10, wherein a pH of the slurry that was neutralized ranges from about 6.9 to about 8.5.

14. The method of claim 1, wherein a temperature of the slurry that was neutralized ranges from about 25° C. to about 47° C.

15. The method of claim 14, wherein a temperature of the slurry that was neutralized ranges from about 28° C. to about 32° C.

16. The method of claim 1, wherein the method further comprises drying the slurry to isolate the precipitated $CaCO_3$ and form dried $CaCO_3$.

17. The method of claim 16, wherein the method further comprises combining the dried $CaCO_3$ with an oral care ingredient to form an oral care composition.

* * * * *